United States Patent [19]
Nakanishi

[11] Patent Number: 5,692,903
[45] Date of Patent: Dec. 2, 1997

[54] EXCHANGEABLE CARTRIDGE FOR DENTAL HANDPIECE

[75] Inventor: Takasuke Nakanishi, Kanuma, Japan

[73] Assignee: Nakanishi, Inc., Tochigi-Ken, Japan

[21] Appl. No.: 593,504

[22] Filed: Jan. 30, 1996

[30] Foreign Application Priority Data

Feb. 6, 1995 [JP] Japan .................. 7-000363 U

[51] Int. Cl.$^6$ ................... A61C 1/02; A61C 17/00
[52] U.S. Cl. .......................... 433/116; 433/115
[58] Field of Search ...................... 433/115, 116

[56] References Cited

U.S. PATENT DOCUMENTS

| Re. 35,147 | 1/1996 | Apap et al. | 433/116 |
|---|---|---|---|
| 1,678,097 | 7/1928 | Andresen | 433/115 |
| 3,098,299 | 7/1963 | Page | 433/115 |
| 4,225,308 | 9/1980 | Lohn | 433/115 |
| 4,975,056 | 12/1990 | Eibofner | 433/115 |
| 5,252,065 | 10/1993 | Nakanishi | 433/115 |
| 5,423,678 | 6/1995 | Nakanishi | 433/115 |

FOREIGN PATENT DOCUMENTS

| 920096 | 3/1963 | United Kingdom | 433/115 |
|---|---|---|---|

Primary Examiner—Paul L. Hirsch
Attorney, Agent, or Firm—Malcolm B. Wittenberg

[57] ABSTRACT

An exchangeable cartridge for a dental handpiece includes first dust-proofing members for preventing foreign matter from being intruded into an upper bearing and second dust-proofing members for preventing foreign matter from being intruded into a lower bearing. The first dust-proofing members have an upper rotational partitioning member and an upper fixed partitioning member. The upper rotational partitioning member has a protrusion provided above the upper bearing and protruding radially outwardly. The upper fixed partitioning member has a radially inwardly protruding portion lying adjacent and parallel to the protrusion of the upper rotational partitioning member to define a first interstice leading to the upper bearing. The second dust-proofing members have a lower rotational partitioning member and a lower fixed partitioning member. The lower rotational partitioning member has a protrusion provided below the lower bearing and protruding radially outwardly. The lower fixed partitioning member has a radially inwardly protruding portion lying adjacent and parallel to the protrusion of the lower rotational partitioning member to define a second interstice leading to the lower bearing.

4 Claims, 2 Drawing Sheets

EXCHANGEABLE CARTRIDGE FOR DENTAL HANDPIECE

BACKGROUND OF THE INVENTION

This invention relates to an exchangeable cartridge for a dental handpiece, and in particular a cartridge exchangeably loaded in a head part of a dental handpiece, such as an angle type dental handpiece.

In a dental handpiece, a variety of dust-proofing measures have been used to protect bearings from foreign matter, such as dusts or cut tooth debris. In Japanese Utility Model Laid-Open Application No. 4-88922 (1992), the foreign matter unavoidably sucked into the inside of the handpiece is blown circumferentially outwards by rotation of a rotating partitioning member for prohibiting such foreign matter from being intruded into the inside of the bearings. However, no such dust-proofing measures have been used in a cartridge exchangeably loaded within a head part of a dental handpiece, particularly an angle type dental handpiece.

In addition, the conventional dust-proofing means is mainly employed for protecting the lower bearing positioned near an opening for rotatably receiving a dental treatment tool. However, the conventional dust-proofing means suffers from a problem that the foreign matter is liable to be intruded via a narrow gap into the upper bearing positioned near a head cap of the head part of a dental handpiece.

SUMMARY OF THE INVENTION

It is therefore an object of the present invention to provide an exchangeable cartridge for a dental handpiece capable of preventing the upper bearing and the lower bearing from foreign matter such as dusts or cut tooth debris being intruded.

It is another object of the present invention to provide an exchangeable cartridge for a dental handpiece having in the exchangeable cartridge itself dust-proofing means which is simple in structure and which can be easily manufactured.

The above and other objects of the invention will become apparent from the following description.

According to the present invention, there is provided an exchangeable cartridge for a dental handpiece including rotational means for removably receiving and rotationally driving a dental treatment tool, an upper bearing and a lower bearing for rotationally supporting the rotational means, a rotor mounted on the rotational means for rotating the rotational means by means of pressurized air, a casing for fixedly supporting the upper bearing and the lower bearing, first dust-proofing means provided adjacent to the upper bearing and second dust-proofing means provided adjacent to the lower bearing. The first dust-proofing means includes an upper rotational partitioning member and an upper fixed partitioning member. The upper rotational member has a protrusion provided above the upper bearing and protrudes radially outwardly. The upper fixed partitioning member has a radially inwardly protruding portion lying adjacent and parallel to the protrusion of the upper rotational partitioning member to define a first interstice leading to the upper bearing. The second dust-proofing means includes a lower rotational partitioning member and a lower fixed partitioning member. The lower rotational partitioning member has a protrusion provided below the lower bearing and protrudes radially outwardly, while the lower fixed partitioning member has a radially inwardly protruding portion lying adjacent and parallel to the protrusion of the lower rotational partitioning member to define a second interstice leading to the lower bearing.

PREFERRED EMBODIMENT OF THE INVENTION

Figure 1:
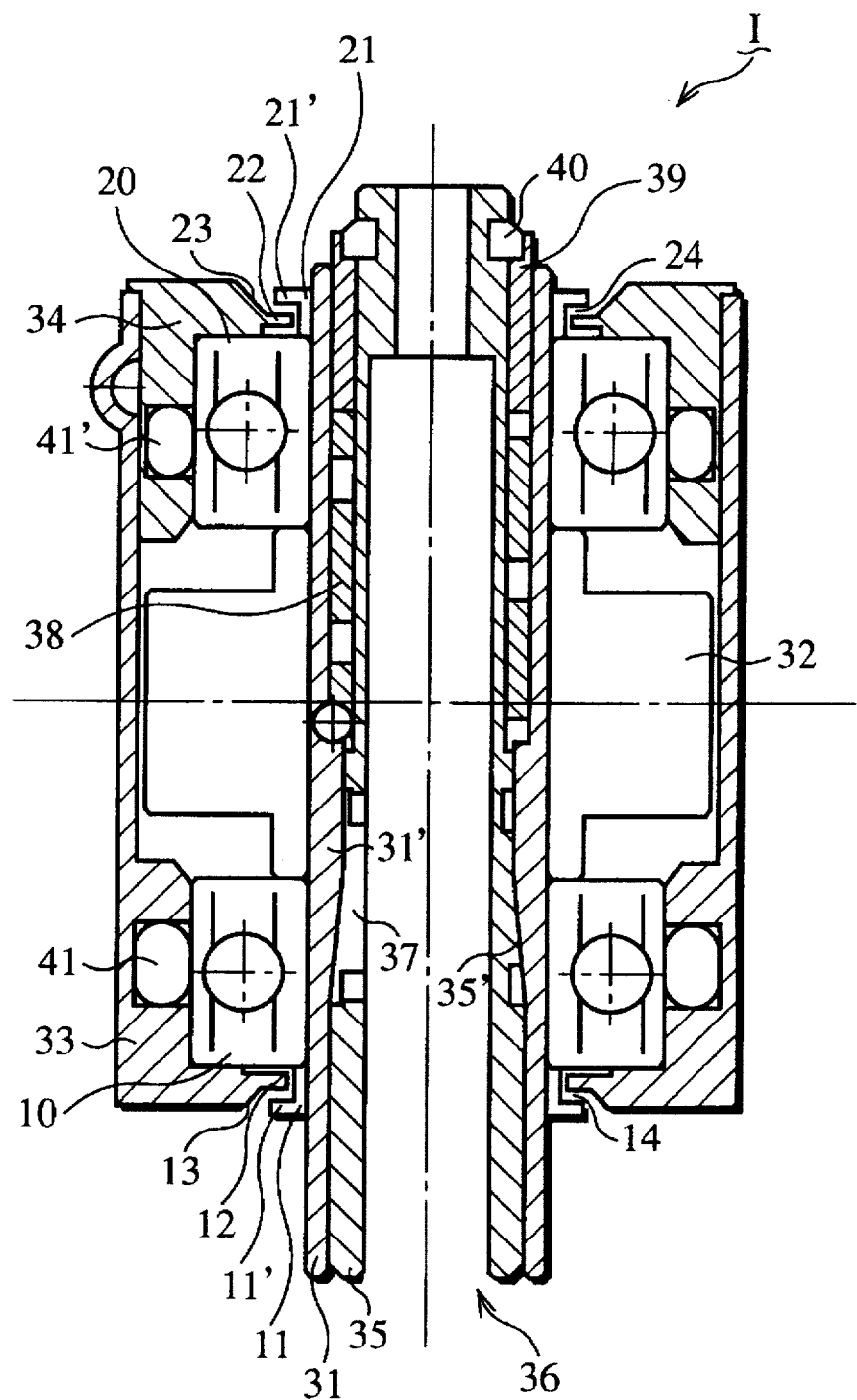
FIG. 1 is a cross-sectional view of a cartridge according to the present invention.

Referring to the drawings, a preferred embodiment of the present invention will be explained in detail.

Figure 2:
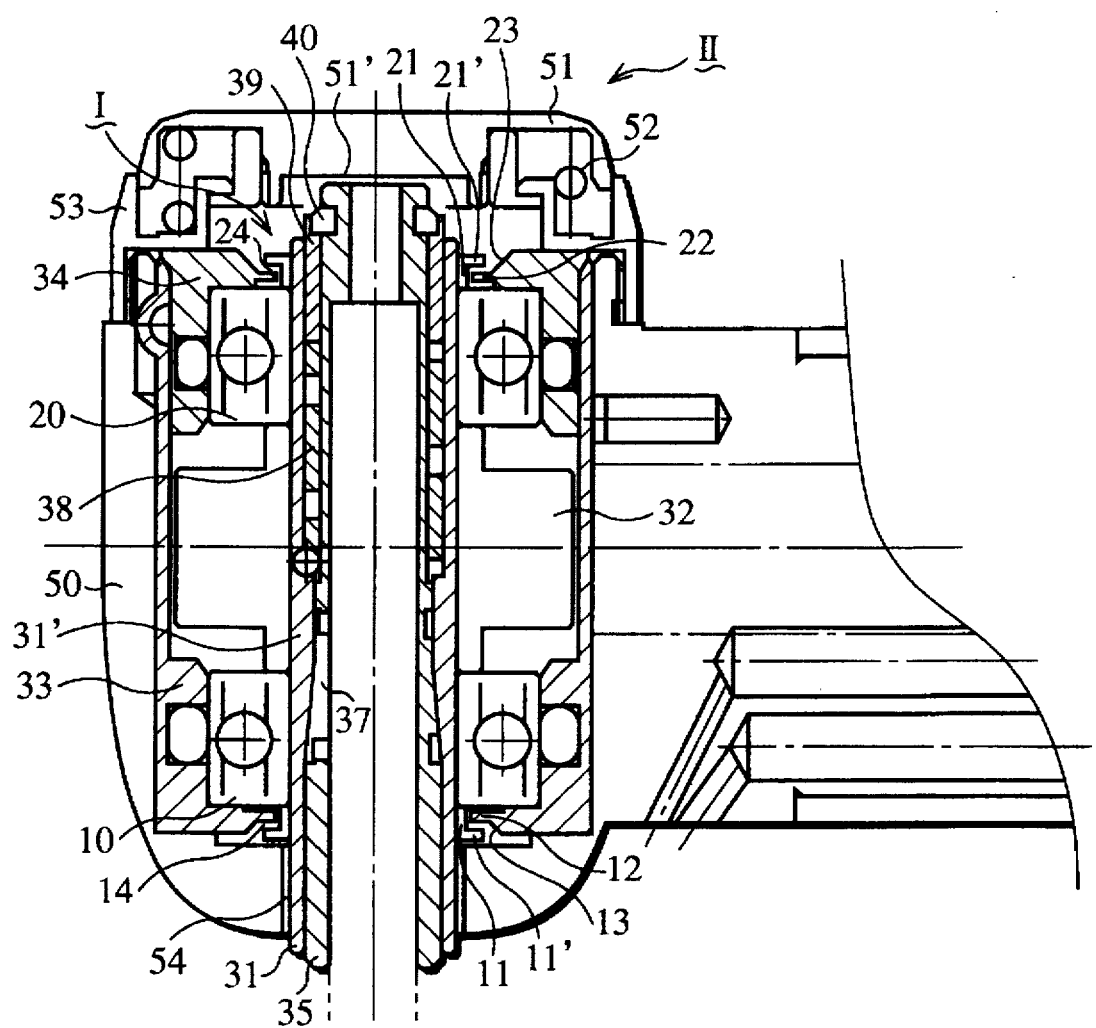
FIG. 2 is a cross-sectional view showing a handpiece head part fitted with the cartridge shown in FIG. 1.

FIG. 1 is an axial cross-sectional view showing a cartridge I of a dental handpiece according to the present invention, and FIG. 2 is a partial cross-sectional view showing a head part II of the handpiece fitted with the cartridge I.

The cartridge I has a rotor shaft 31 operating as a rotary shaft member, a bur holder 35 fitted into the rotor shaft 31 for receiving a dental treatment tool, not shown, through an opening 38 of the bur holder 35, a lower bearing 10 and an upper bearing 20 for supporting the rotor shaft 31, and a rotor 32 secured to the outer circumferential surface of the rotor shaft 31 between the bearings 10 and 20 for rotationally driving the rotor shaft 31 under the effect of pressurized air. The cartridge I also has a cartridge casing 33 for holding the lower bearing 10 and the upper bearing 20 via O-rings 41, 41' and a casing lid 34 for covering the upper bearing 20. Although not shown, an opening for air intake and air discharge is provided in the cartridge casing 33.

The rotor shaft 31 is progressively reduced in diameter towards above on its inner circumferential surface and then maintained at a constant diameter to form a thickened portion 31'. The bur holder 35 has a tapered surface 35' progressively increased in outer diameter towards below and a bur setting pin 37 built in a portion of the tapered surface 35', as shown in FIG. 1. Thus, when the dental treatment tool is introduced into the inside of the bur holder 35, the holder 35 rides on the thickened portion 31' of the rotor shaft 31, and is then reduced in diameter so that the tool is secured by being pressed by the setting pin 37.

For dismounting the dental treatment tool, a pushbutton 51 (see FIG. 2) is pressed downwards against the force of a spring 52. This causes a bottom surface 51' of the pushbutton 51 to thrust the bur holder 35 downwards, with the tapered surface 35' and the bur setting pin 37 being slipped off the thickened portion 31' to release the setting of the tool.

The bur holder 35 thus pressed down is restored upwards under the force of a spring plate 38 provided between the holder 35 and the rotor shaft 31 and mounted on a spring retainer 39 and a split ring 40 for fixing the retainer 39.

The aforementioned mechanism for attaching and detaching the dental treatment tool is well known in the art and thus is not explained further in detail herein.

The cartridge I is also provided with dust-proofing means for protecting the lower bearing 10 and the upper bearing 20 against foreign matters such as dusts or cut tooth debris. The dust-proofing means is comprised of upper and lower rotational partitioning members 11, 21 of L-shaped cross sections secured to the outer circumferential surfaces of the rotor shaft 31, and fixed lower and upper partitioning members 12, 22 respectively provided on the cartridge casing 33 and the casing lid 34, as shown in FIG. 1.

The rotational partitioning members 11, 21 are respectively provided with radially outwardly extending protrusions 11', 21' to extend radially parallel to the lower side of the lower bearing 10 and the upper side of the upper bearing 20, respectively. The fixed partitioning members 12, 22 are protruded radially inwardly between the protrusions 11', 21' and the bearings 10, 20, respectively to define passages leading to the bearings 10, 20 in the form of interstices 14, 24 of U-shaped cross-sections, respectively.

The cartridge casing 33 and the casing lid 34 are provided respectively with inclined surfaces 13, 23 at the proximal ends of the respective fixed partitioning members 12, 22 to define larger openings between the fixed partitioning members 12, 22 and the protrusions 11', 21', respectively, as shown in FIG. 1.

With the above-described cartridge I, if the foreign matter such as dusts or cut tooth debris is sucked during dental treatment into the inside of the head part II via an interstice 54 (see FIG. 2) between the rotor shaft 31 and a head housing jacket 50, such foreign matter is blown off by the protrusion 11' circumferentially by rotation of the rotational partitioning member 11 for prohibiting intrusion of the foreign matter into the inside of the bearing 10, with the inclined surface 13 then assisting to blow off the foreign matter.

Meanwhile, the aforementioned dust-proofing means does not simply serve to blow off the foreign matter. Since the rotational velocity becomes maximum at the radially outwardly positioned end of the protrusion 11' during rotation of the rotational partitioning member 11, the air pressure becomes minimum near the inlet portion of the interstice 14. Thus, the foreign matter cannot be intruded into the interstice 14, and into the bearing 10, where the air pressure becomes higher.

During dental treatment, the foreign matter tends to be intruded via a gap between a head cap 53 and the pushbutton 51. However, the upper rotational partitioning member 21 and the fixed upper partitioning member 22 operate in a similar manner to the above-described lower dust-proofing means for preventing the foreign matter from being intruded into the upper bearing 20.

According to the present invention, since the dust-proofing means is provided in the cartridge itself, the bearings in the dental handpieces of all types fitted with the cartridge can be protected against the foreign matter such as dusts or cut tooth debris. Since the dust-proofing means is provided not only for the lower bearing but also for the upper bearing, the foreign matter cannot be intruded into the upper bearing for which no suitable protecting measures have been taken in the conventional dental handpiece.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. An exchangeable cartridge for a dental handpiece comprising:

rotational means for removably receiving and rotationally driving a dental treatment tool;

an upper bearing and a lower bearing for rotationally supporting said rotational means;

a rotor mounted on said rotational means for rotating said rotational means by means of pressurized air;

a casing for fixedly supporting said upper bearing and the lower bearing;

first dust-proofing means provided adjacent to said upper bearing; and second dust-proofing means provided adjacent to said lower bearing;

said first dust-proofing means having an upper rotational partitioning member and an upper fixed partitioning member, said upper rotational partitioning member having a protrusion provided above the upper bearing and protruding radially outwardly, said upper fixed partitioning member having a radially inwardly protruding portion lying adjacent and parallel to said protrusion of said upper rotational partitioning member to define a first interstice leading to said upper bearing;

said second dust-proofing means having a lower rotational partitioning member and a lower fixed partitioning member, said lower rotational partitioning member having a protrusion provided below the lower bearing and protruding radially outwardly, said lower fixed partitioning member having a radially inwardly protruding portion lying adjacent and parallel to said protrusion of said lower rotational partitioning member to define a second interstice leading to said lower bearing.

2. The exchangeable cartridge according to claim 1 wherein said casing comprises a casing main body for supporting said upper bearing and said lower bearing and a casing lid covering said casing main body, said upper fixed partitioning member being integrally formed with said casing lid and said lower fixed partitioning member being integrally formed with said casing main body.

3. The exchangeable cartridge according to claim 1 wherein the upper fixed partitioning member has an inclined surface tapered radially outwardly towards above to define a large opening of said first interstice.

4. The exchangeable cartridge according to claim 1 wherein the lower fixed partitioning member has an inclined surface tapered radially outwardly towards below to define a large opening of said second interstice.

* * * * *